(12) United States Patent
Laghi

(10) Patent No.: US 12,343,945 B2
(45) Date of Patent: Jul. 1, 2025

(54) METHOD OF MAKING A NOVEL SILICONE LINER

(71) Applicants: Alps South Euruope, s.r.o., Plzen (CZ); Aldo Laghi, Pinellas Park, FL (US)

(72) Inventor: Aldo Laghi, Pinellas Park, FL (US)

(73) Assignee: Alps South Europe, S.R.O.

( * ) Notice: Subject to any disclaimer, the term of this patent is extended or adjusted under 35 U.S.C. 154(b) by 320 days.

(21) Appl. No.: 17/741,667

(22) Filed: May 11, 2022

(65) Prior Publication Data

US 2022/0281181 A1 Sep. 8, 2022

Related U.S. Application Data

(62) Division of application No. 16/868,776, filed on May 7, 2020, now Pat. No. 11,602,445.

(60) Provisional application No. 62/844,253, filed on May 7, 2019, provisional application No. 62/844,296, filed on May 7, 2019.

(51) Int. Cl.
*B29C 70/30* (2006.01)
*B29C 33/38* (2006.01)
*B29C 70/54* (2006.01)
*B29K 83/00* (2006.01)
*B29L 31/00* (2006.01)

(52) U.S. Cl.
CPC .......... *B29C 70/30* (2013.01); *B29C 33/3842* (2013.01); *B29C 70/54* (2013.01); *B29K 2083/00* (2013.01); *B29L 2031/7532* (2013.01)

(58) Field of Classification Search
CPC ......... B29C 33/40; B29C 33/405; A61F 2/72; A61F 2/7812; A61F 2/80; A61F 2/582; A61F 2/60; A61F 2002/30563; A61F 2002/5003; A61F 2002/5053; A61F 2002/7837; A61F 2/5046; A61F 2/54; Y10S 264/30; Y10S 623/90

See application file for complete search history.

(56) References Cited

U.S. PATENT DOCUMENTS

| | | | |
|---|---|---|---|
| 4,923,474 A | 5/1990 | Klasson | |
| 5,443,525 A | 8/1995 | Laghi | |
| 5,507,834 A | 4/1996 | Laghi et al. | |
| 5,728,168 A | 3/1998 | Laghi | |
| 5,830,237 A | 11/1998 | Kania | |

(Continued)

OTHER PUBLICATIONS

Harmon, How to Improve Your Sandblasting Speed & Production, Feb. 28, 2019 (from Internet Archive; accessed Mar. 19, 2024) https://pittsburghsprayequip.com/blogs/pittsburgh-spray-equipment-company/improve-sandblasting-speed (Year: 2019).*

(Continued)

*Primary Examiner* — Andrew L Swanson
(74) *Attorney, Agent, or Firm* — Carlson IP Law

(57) ABSTRACT

A silicone prosthetic liner for use with a prosthetic assembly that acts as the interface between the residual limb of an amputee and the socket assembly. The prosthetic liner comprises an open proximal end, a closed distal end, and sidewalls comprising an inner layer of molded silicone. The silicone is molded over a mandrel that has been sandblasted using #36 grit and, optionally, #320 grit at 100 psi so as to form microcraters and reduce the coefficient of static friction.

7 Claims, 5 Drawing Sheets

Section 3-3

(56) References Cited

U.S. PATENT DOCUMENTS

| | | | | |
|---|---|---|---|---|
| 2002/0002405 A1* | 1/2002 | Janusson | .............. | B29D 23/001 |
| | | | | 623/36 |
| 2006/0111485 A1* | 5/2006 | Laghi | ....................... | C08K 5/01 |
| | | | | 523/122 |
| 2012/0041568 A1* | 2/2012 | Mackenzie | ........... | A61F 2/5046 |
| | | | | 623/36 |
| 2019/0142574 A1* | 5/2019 | Quirós | ..................... | A61L 27/18 |
| | | | | 623/8 |

OTHER PUBLICATIONS

Harmon, How to Improve Your Sandblasting Speed & Production, Feb. 28, 2029 (from Internet Archive; accessed Mar. 19, 2024); https://pittsburghsprayequip.com/blogs/pittsburgh-spray-equipment-company/improve-sandblasting-speed (Year: 2019).*

* cited by examiner

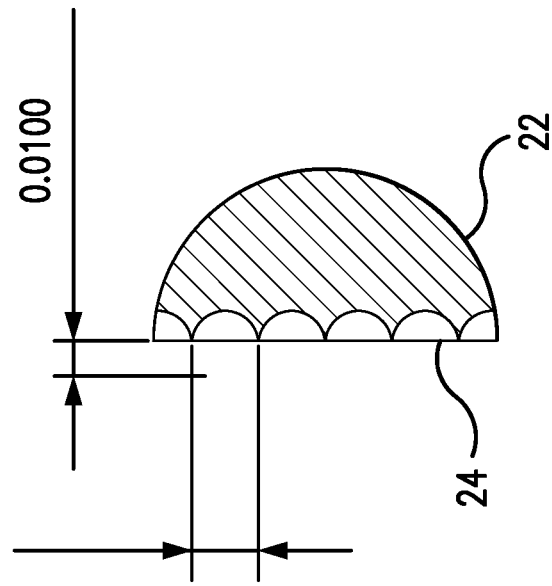
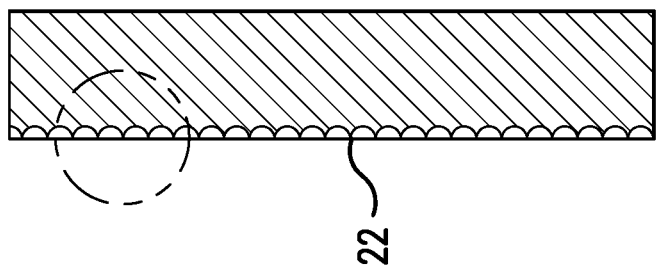
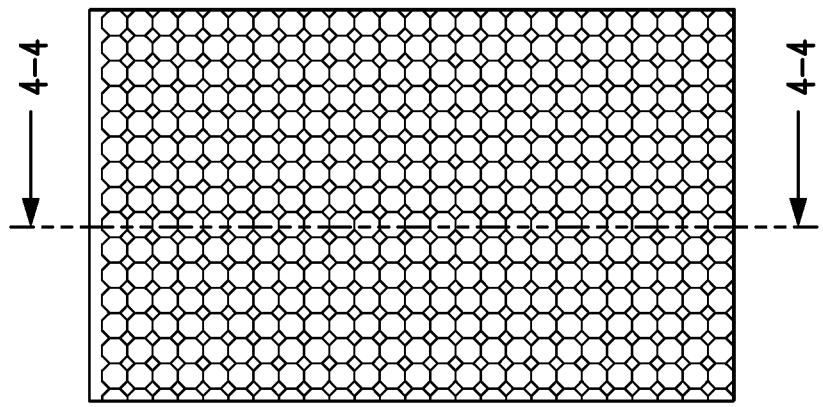
Section 4-4
FIG. 4

METHOD OF MAKING A NOVEL SILICONE LINER

CROSS-REFERENCE TO RELATED APPLICATIONS

This application is a divisional of application Ser. No. 16/868,776, filed May 7, 2020 entitled "Novel Silicone Liner", which claimed the benefit of provisional application No. 62/844,253, filed May 7, 2019, and provisional application No. 62/844,296, filed May 7, 2019, the disclosures of which are incorporated by reference herein.

BACKGROUND OF THE INVENTION

Field of the Invention

This invention relates to liners for use in a prosthetic assembly. Specifically, the described invention relates to liners having a silicone lining that is smooth to the touch via the use of sand-blasting the molds used to create the liners.

Description of the Background Art

Silicone liners have been used since the 1980s in the prosthetic industry such as those described in U.S. Pat. No. 4,923,474 granted to Klasson and Kristinsson. Other examples of such liners include U.S. Pat. No. 5,728,168 to Laghi et al., U.S. Pat. No. 5,830,237 granted to Kania, U.S. Pat. No. 5,507,834 to Laghi et al., U.S. Pat. No. 5,443,525 to Laghi et al., and U.S. Pat. No. 5,728,168 to Laghi et al.

However, silicone liners have historically been difficult to don and doff due to the high coefficient of static friction of silicone. As such, they tend to stick to the skin of a residual limb. This prevents relative movement at the interface skin/liner and therefore induces high shear forces on the skin in localized portions of the residual limb as the ground reaction to ambulation is transmitted to the skeleton through the silicone interface and the skin. These resulting shear forces increase the likelihood of blistering of the skin, especially for patients with sensitive skin. It is therefore desired to develop a silicone liner having a reduced frictional effect such that the user can easily don and doff their prosthetic liner.

Further, most amputees have had amputations for vascular, as opposed to traumatic, reasons. This means that the amputation was because of poor circulation. Most amputees are also elderly. As such, most amputees have thinner, more delicate, skin which is prone to damage and have reduced blood flow to the extremities giving them less ability to heal sores and wounds. Some elderly amputees end up having recurring amputations as the skin of their residual limbs becomes damaged and infected.

One method that has been developed to thwart these issues is to include additives that exude from the silicone matrix and act as a lubricant between the liner and skin. The issue with this solution is that the exudate can collect dirt on the inside surface of the liner, exacerbating skin damage. Exudates also require more thorough cleaning and make the liner slippery.

The present invention utilizes a novel sandblasting technique so as to create "microcraters" in the silicone of the prosthetic liner, as it is molded, which allow for the liner to be donned and doffed with ease and which is skin-friendly. The method described herein is particularly effective for silicone liners because silicones, when in the liquid state, have low surface tension which allows them to penetrate tiny holes and cracks and, therefore, to create the microcraters. Silicones' viscosity is also inversely proportional to temperature which makes silicone flow easier as they get closer to the surface of the hot mold. As a result, silicones produce a faithful mirror image of the cratered mold surface.

Therefore, it is an object of this invention to provide an improvement which overcomes the aforementioned inadequacies of the prior art devices and provides an improvement which is a significant contribution to the advancement of the liner art.

Another object of the invention is to provide a silicone liner with a more comfortable interior silicone lining.

Another object of the invention is to provide a method of manufacturing silicone liners having reduced frictional characteristics.

Another object of the invention is provide a liner having microcraters.

Another object of the invention is to describe a method of making silicone liners by molding the liners using mold mandrels that have been sandblasted.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The present invention relates generally to a liner for use in a prosthetic assembly having a silicone interior comprising microcraters by sandblasting the silicone mandrel using #36 grit at 100 psi. Using a sandblasted mold mandrel, a silicone liner can be manufactured having improved friction characteristics. The liner of the present invention may optionally include a fabric cover bonded to the exterior surface.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which:

FIG. 4 is a sectional view of a silicone sheet formed using a mandrel sandblasted with #320 grit at 100 psi.

Similar reference numerals refer to similar parts throughout the several views of the drawings.

DETAILED DESCRIPTION OF THE PREFERRED EMBODIMENT

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1:
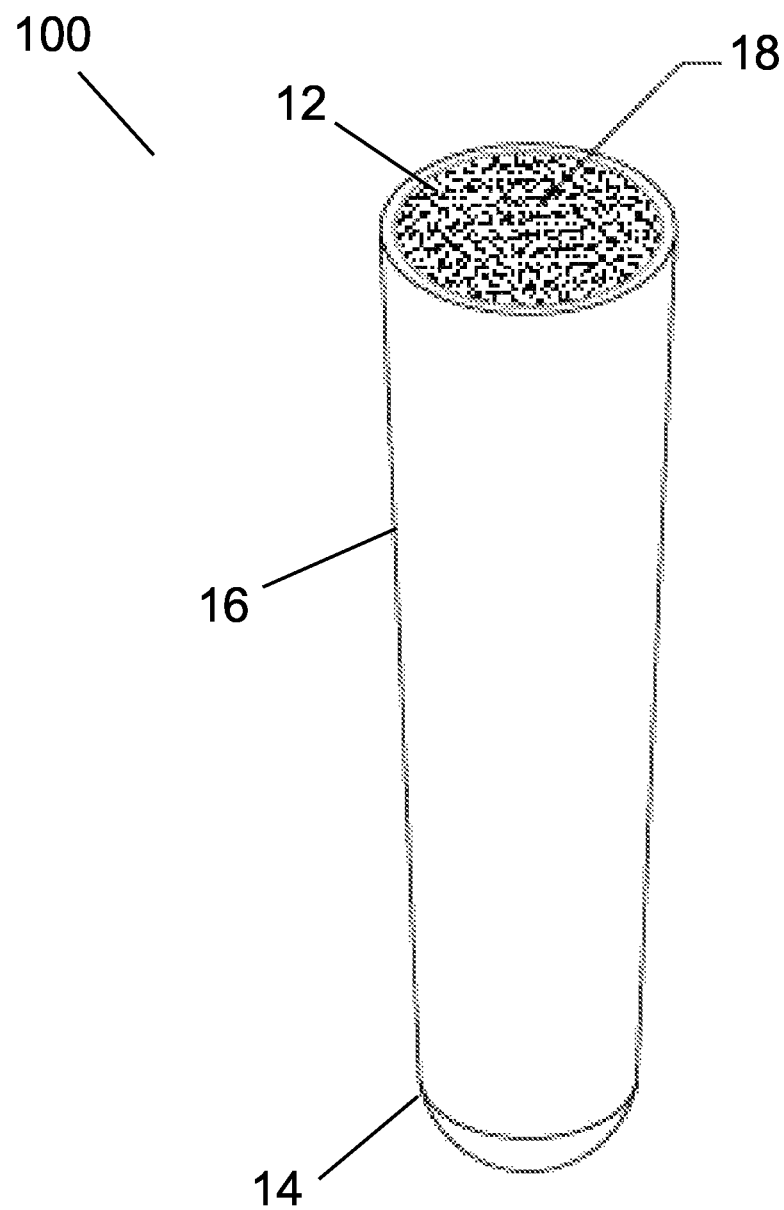
FIG. 1 is a front view of the improved silicone liner.

The present invention relates to a liner 100 for use with prosthetic devices. As shown in FIG. 1, the liner 100 for use with a prosthetic assembly comprises an open upper end 12 for receiving a residual limb, not shown, a closed bottom end 14, and sidewalls 16 of predetermined thickness. The liner is airtight when donned over a residual limb. The preferred thickness of the sidewalls 16 is about 1.5 mm to 3.0 mm. Note that the thickness is greater at the bottom end than in the sidewalls; the preferred thickness of the silicone at said bottom end 14 is about 3.0 mm to 12.0 mm. The sidewalls 16 have an inner layer 18 of the improved silicone described herein. The sidewalls 16 can be fabric or another layer of more durable and higher friction silicone.

Figure 2:
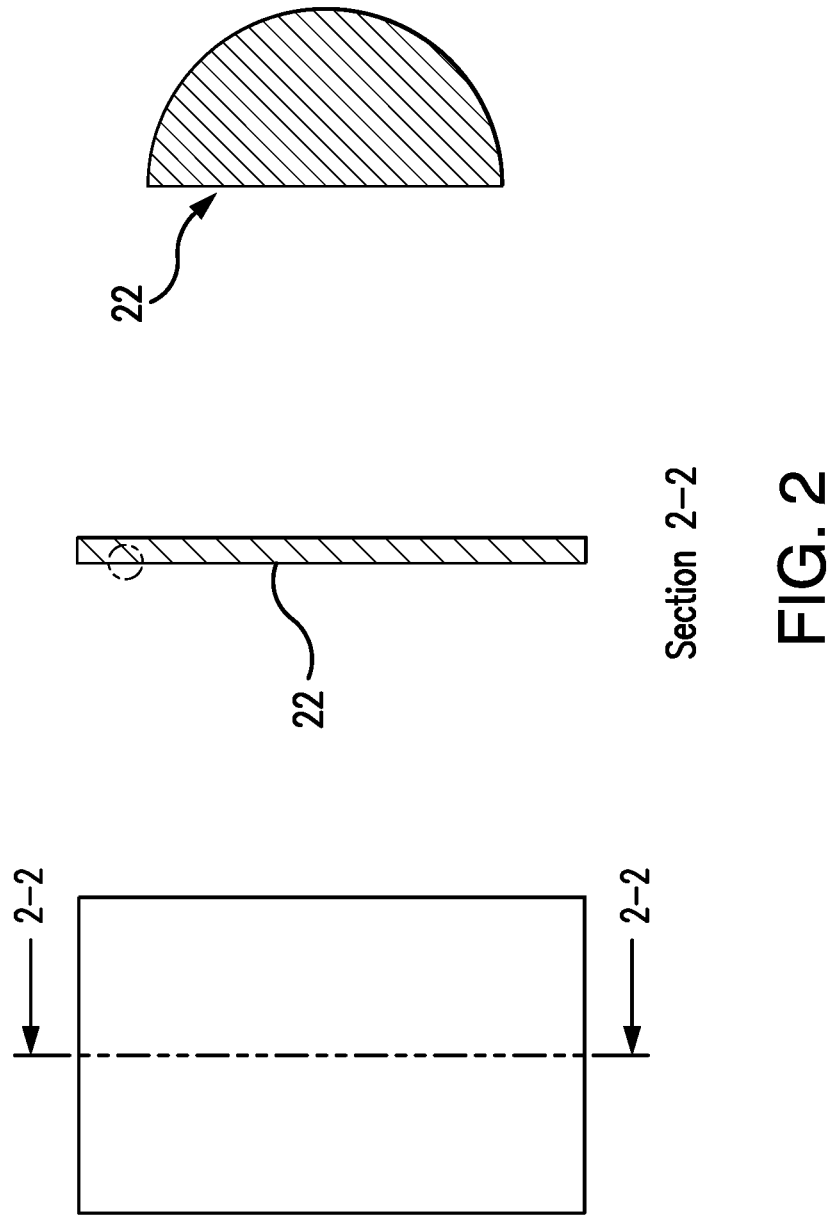
FIG. 2 is a sectional view of a silicone sheet formed using a mandrel that has not been sandblasted.
Figure 3:
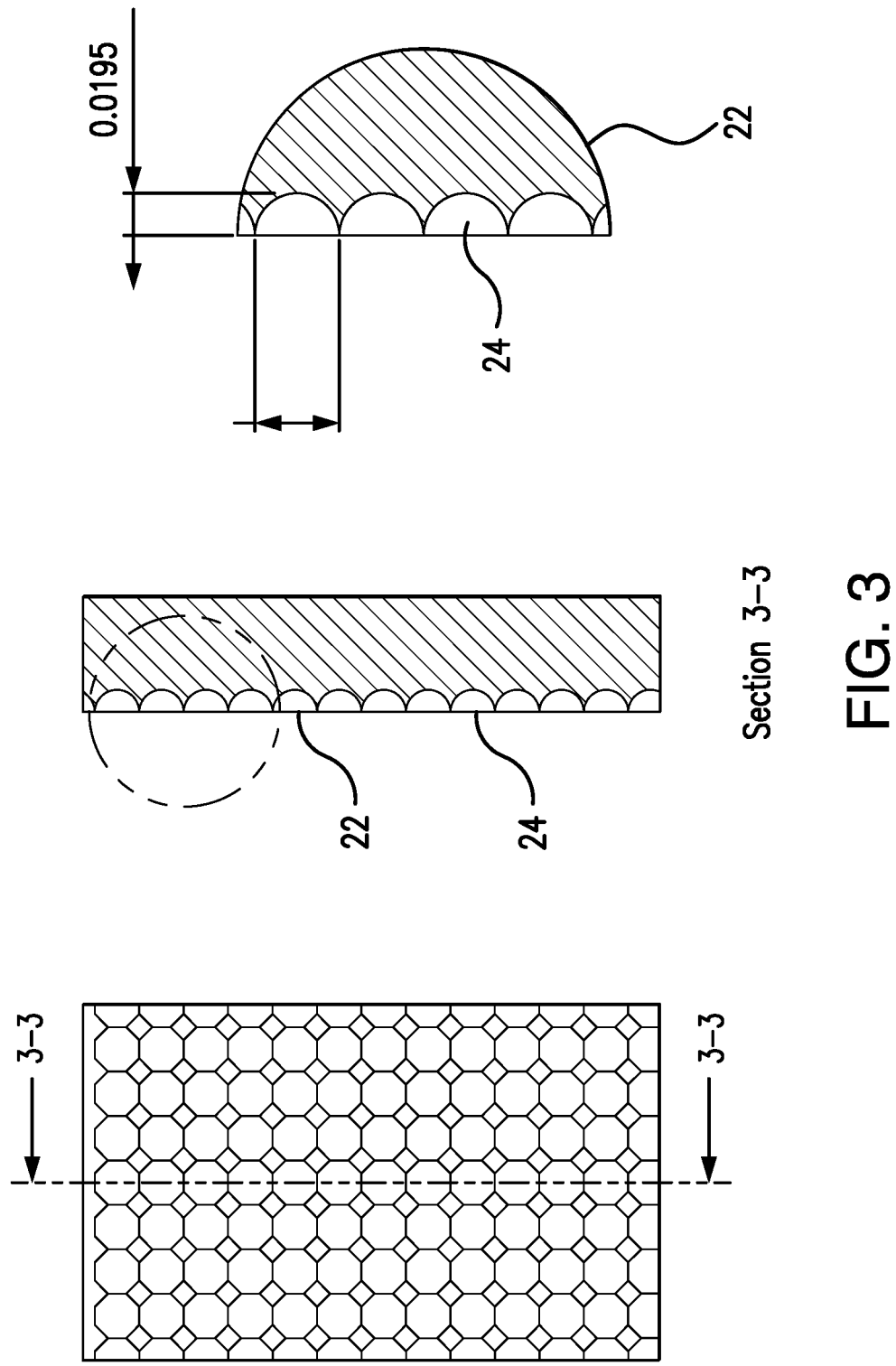
FIG. 3 is a sectional view of a silicone sheet formed using a mandrel sandblasted with #36 grit at 100 psi.

Prior to molding the silicone, a mandrel is sandblasted using #36 grit at 100 psi. The particular grit and pressure used provide the beneficial characteristics of the present invention. Other grits and pressures did not produce the benefits of reduced frictional hold and less chance of skin irritation. After sandblasting the mandrel, the silicone is molded over it, allowing the silicone to seep into the microcraters formed by the sandblasting. As can be seen in FIGS. 2-4, the size of grit used during sandblasting has a sizeable effect.

FIG. 2 depicts a sheet of silicone 20 that has not been sandblasted. As can be seen by the cross-section 2-2, not sandblasting the mandrel results in a smooth exterior surface 22 which maintains the high frictional characteristics of silicone. FIGS. 3 and 4, on the other hand, show a microscopic view of exterior surface 22 after having the mandrel sandblasted. FIG. 3 shows the microcratering the exterior surface 22 is subjected to using #36 grit at 100 psi. Along line 3-3, the microcraters created generally have a depth of about 0.0195 mm. FIG. 4 shows the microcratering the exterior surface 22 is subjected to using #320 grit at 100 psi. Along line 4-4, the microcraters created generally have a depth of about 0.0100 mm. The deeper microcraters create a lower static coefficient of friction for silicone because there is less surface area for the exterior surface 22 to be in contact with, as can be seen when comparing the sheet in FIG. 3 with the sheet in FIG. 4.

Figure 5:
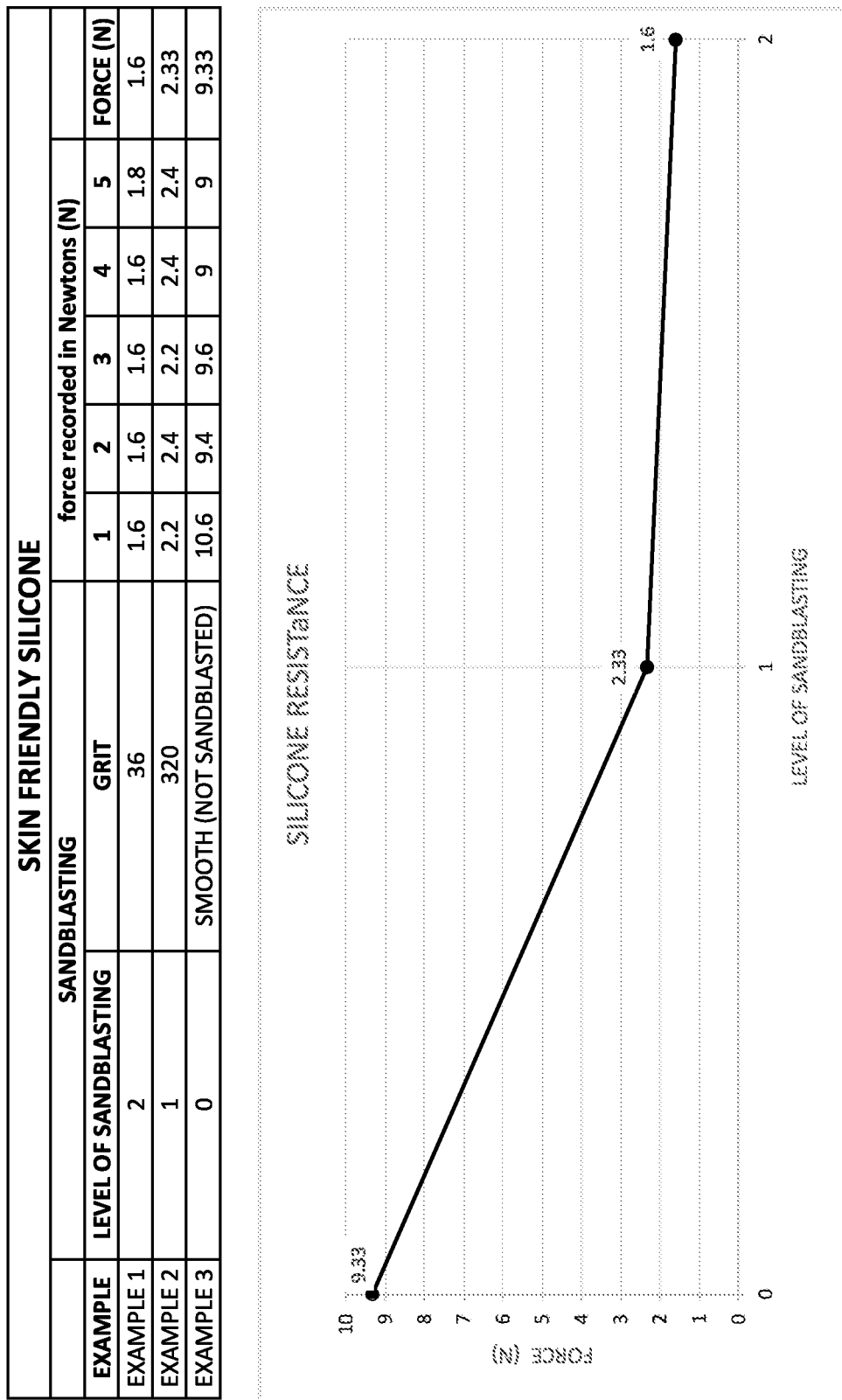
FIG. 5 is a graph showing the effect of sandblasting on the pulling force necessary to remove a silicone sheet from a steel substrate showing the effect on the static coefficient of friction.

Three tests were performed to exhibit the beneficial properties of the present invention, the results of which are shown in FIG. 5. In the first, the mold was sandblasted using #36 grit at 100 psi and it took 1.6 N of force in terms of pull resistance. In the second test, the mold was sandblasted using #320 grit. The result was 2.33 N of force in terms of pull resistance. In the final test the mold was not sandblasted at all and required 9.33 N of force. The tests were performed on smooth stainless steel using silicone strips that were 1 inch wide and 7 inches long while applying 100 grams of weight.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A method of making a silicone liner comprising;
sandblasting a mandrel with #36 grit at 100 psi;
molding silicone over the mandrel;
forming fabric sidewalls over the silicone creating a composite wherein the composite further comprises an open upper end, a closed bottom end, and fabric sidewalls having a thickness wherein said fabric sidewalls further comprises a layer of silicone only on an interior side of the fabric sidewalls having a silicone thickness wherein said silicone has microcraters having a depth of about 0.0195 millimeters.

2. The method of making a silicone liner of claim 1 wherein the thickness of the sidewalls is between 1.5 and 3 millimeters.

3. The method of making a silicone liner of claim 1 wherein the silicone thickness at the bottom end is between 3 and 12 millimeters.

4. The method of making a silicone liner of claim 1 wherein the mandrel is sandblasted with #320 grit at 100 psi after sandblasting with #36 grit but before molding.

5. A method of making a silicone liner comprising:
sandblasting a mandrel with #320 grit at 100 psi;
molding silicone over the mandrel;
forming fabric sidewalls over the silicone creating a composite wherein the composite further comprises an open end, a closed bottom end, and fabric sidewalls having a thickness wherein said fabric sidewalls further comprise a layer of silicone only on an interior side of the fabric sidewalls having a silicone thickness wherein said silicone has microcraters having a depth of about 0.0100 millimeters.

6. The method of making a silicone liner of claim 5 wherein the silicone thickness at the bottom end is between 3 and 12 millimeters.

7. The method of making a silicone liner of claim 5 wherein the thickness of the sidewalls is between 1.5 and 3 millimeters.

* * * * *